United States Patent [19]

Laza et al.

[11] Patent Number: 5,580,869
[45] Date of Patent: Dec. 3, 1996

[54] 1N SUBSTITUTED PYRAZINO[2,3-C]-1,2,6-THIADIAZINE 2,2-DIOXIDES

[75] Inventors: Pilar G. Laza, Majadahonda; Juan A. Paez Prosper, Madrid; Emilio Carrasco Yufera; Manuel Grau Mateo, both of Barcelona, Spain

[73] Assignees: Prodesfarma, S.A., Barcelona; Consejo Superior de Investigaciones Cientificas, Madrid, both of Spain

[21] Appl. No.: 93,256

[22] Filed: Jul. 16, 1993

[30] Foreign Application Priority Data

Jul. 22, 1992 [ES] Spain .................................... 9201532

[51] Int. Cl.$^6$ ........................ A61K 31/54; C07D 513/04
[52] U.S. Cl. ............................................. 514/222.8; 544/10
[58] Field of Search ............................ 514/222.8; 544/10

[56] References Cited

FOREIGN PATENT DOCUMENTS

| | | |
|---|---|---|
| 0286041 | 2/1988 | European Pat. Off. . |
| 8507559 | 3/1984 | Spain . |
| 8604193 | 6/1984 | Spain . |
| 2009198 | 9/1989 | Spain . |
| 2160519 | 12/1985 | United Kingdom . |

OTHER PUBLICATIONS

Journal of Heterocyclic Chemistry, vol.27,No.3,1990, Provo,U.S., pp. 785–786 P. Goya et al. "Reactivity of 4–amino–6,7–diphenyl–8H–pyrazino(2–3–c)–1,2,6–thiadiazine 2,2–dioxide towards methylating agents".

Liebigs Annalen Der Chemie,No.3,1991, Weinheim,Germany, pp. 301–303 I. Alkorta et al. "Pyrazino(2–3–c)thiadiazine, 2,2–dioxides. Synthesis of SO$_2$ analogues of folic acid antagonists".

Heterocycles, vol. 27, No.9, 1988, Amsterdam, Netherlands, pp. 2201–2211 P. Goya et al. "Tautomerism in pyrazino(2,3–c)–1,2,6–thiadiazine 2,2–dioxides".

Liebigs Annalen Der Chemie, No.2,1988, Weinheim, Germany, pp. 121–124 P.Goya et al. "Pteridine analogues; Synthesis and physico–chemical properties of 7–oxopyrazino(2,3–c)(1,2,6)thiadiazine 2,2–dioxides".

Chemical Abstracts, vol.106, No.1, 1987, Columbus, Ohio, U.S., Abstract No. 5092y, L.Goya et al. "Pyrazinothiadiazine S,S–dioxides", page 479.

J. Heterocyclic Chem., 25 pp. 891–893 (1988).

Journal of Photochemistry and Photobiology. A. Chemistry, 53 (1990) pp. 293–300.

Goya et al., Chemical Abstracts, vol. 117, entry 212458q (1992).

Goya et al., Chemical Abstracts, vol. 113, entry 115264h (1990).

Goya et al., Chemical Abstracts, vol. 110, entry 211978c (1989).

Goya et al., Chemical Abstracts, vol. 101 entry 230491u (1984).

Primary Examiner—John M. Ford
Attorney, Agent, or Firm—McAulay Fisher Nissen Goldberg & Kiel, LLP

[57] ABSTRACT 1N substituted pyrazino[2,3-c]-1,2,6-thiadiazine 2,2-dioxides of formula I

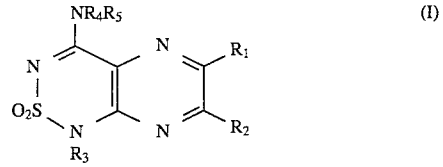

where:

$R_1$ and $R_2$, which may be the same or different, are members of the group formed by hydrogen, straight or branched chain alkyl, aryl, trifluoromethyl, halogen, oxo, amino, carboxamido and alkoxycarbonyl;

$R_3$ is a member of the group formed by straight or branched chain alkyl, dialkylaminoethyl, aralkyl, alkoxycarbonylmethyl, carboxymethyl and hydroxyethyl; and $R_4$ and $R_5$, which may be the same or different, are members of the group formed by hydrogen, straight or branched chain alkyl and aralkyl, hydroxyalkyl, amino, aminoalkyl, alkylaminoalkyl; and a process for the preparation thereof.

6 Claims, No Drawings

1N SUBSTITUTED PYRAZINO[2,3-C]-1,2,6-THIADIAZINE 2,2-DIOXIDES

DESCRIPTION

This invention relates to 1N substituted pyrazino[2,3-c]-1,2,6-thiadiazine 2,2-dioxide derivatives of formula I

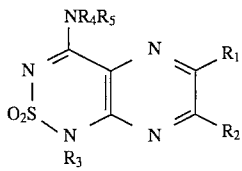

where:

R$_1$ and R$_2$, which may be the same or different, are members of the group formed by hydrogen, straight or branched chain C$_1$–C$_5$ alkyl, aryl, trifluoromethyl, halogen, amino, carboxamido and C$_1$–C$_5$ alkoxycarbonyl or the pharmaceutically acceptable salts thereof with organic or inorganic cations.

R$_3$ is a member of the group formed by straight or branched chain alkyl, dialkylaminoethyl, aralkyl, alkoxycarbonylmethyl, carboxymethyl and hydroxyethyl; and R$_4$ and R$_5$, which may be the same or different, are members of the group formed by hydrogen, straight or branched chain alkyl and aralkyl, hydroxyalkyl, amino, aminoalkyl, alkylaminoalkyl, as well as the organic and inorganic acid salts thereof.

The following compounds are of particular interest from among those of formula I:

4-amino-1-ethyl-6,7-dimethyl-pyrazino[2,3-c]-1,2,6-thiadiazine 2,2-dioxide.

4-amino-1-ethyl-6-phenyl-pyrazino[2,3-c]-1,2,6-thiadiazine 2,2-dioxide.

4-amino-6,7-dimethyl-pyrazino[2,3-c]-1,2,6-thiadiazine-1-[(ethoxycarbonyl)methyl] 2,2-dioxide.

4-amino-6,7-dimethyl-1-(2-morpholinoethyl)-pyrazino[2,3-c]-1,2,6-thiadiazine 2,2-dioxide.

4-methylamino-6-methylpyrazino[2,3-c]-1,2,6-thiadiazine 1,7-diethyl 2,2-dioxide.

4-(2-hydroxyethylamino)-6-methylpyrazino[2,3-c]-1,2,6-thiadiazine 1,7-diethyl 2,2-dioxide.

4-amino-1-[2-(N,N-dimethylamino)ethyl]-6,7-dimethylpyrazino[2,3-c]-1,2,6-thiadiazine 2,2-dioxide.

4-amino-1-[2-(N,N-diisopropylamino)ethyl]-6,7-dimethylpyrazino[2,3-c]-1,2,6-thiadiazine 2,2-dioxide.

4-amino-1,7-diethyl-6-methylpyrazino[2,3-c]-1,2,6-thiadiazine 2,2-dioxide.

4-amino-1-[(ethoxycarbonyl)methyl]-7-phenylpyrazino[2,3-c]-1,2,7-thiadiazine 2,2-dioxide.

4-amino-1-(2-hydroxyethyl)-6,7-dimethylpyrazino[2,3-c]-1,2,6-thiadiazine 2,2-dioxide.

4-amino-1-ethyl-6,7-bis(trifluoromethyl)pyrazino[2,3-c]-1,2,6-thiadiazine 2,2-dioxide.

4-amino-1-ethyl-7-phenylpyrazino[2,3-c]-1,2,6-thiadiazine 2,2-dioxide.

4-amino-6,7-dimethyl-1-propylpyrazino[2,3-c]-1,2,6-thiadiazine 2,2-dioxide.

4-amino-6-bromo-1-ethyl-7-phenylpyrazino[2,3-c]-1,2,6-thiadiazine 2,2-dioxide.

4-amino-1,6,7-triethylpyrazino[2,3-c]-1,2,6-thiadiazine 2,2-dioxide.

4-amino-1-ethyl-6,7,8,9-tetrahydro-1,2,6-thiadiazine[3,4-b]quinoxaline 2,2-dioxide.

4-amino-1-ethyl-6-phenyl-7-methylpyrazino[2,3-c]-1,2,6-thiadiazine 2,2-dioxide.

4-amino-1-ethyl-6-methylpyrazino[2,3-c]-1,2,6-thiadiazine 2,2-dioxide.

4-amino-6-bromo-1-ethyl-7-methylpyrazino[2,3-c]-1,2,6-thiadiazine 2,2-dioxide.

4-amino-1-ethyl-7-phenylpyrazino[2,3-c]-1,2,6-thiadiazine 2,2-dioxide.

4-amino-1-ethyl-6-methyl-7-propylpyrazino[2,3-c]-1,2,6-thiadiazine 2,2-dioxide.

4-amino-7-ethyl-6-methyl-1-propylpyrazino[2,3-c]-1,2,6-thiadiazine 2,2-dioxide.

4-amino-7-ethyl-1,6-dimethylpyrazino[2,3-c]-1,2,6-thiadiazine 2,2-dioxide.

4-amino-1-ethyl-6,7-diisopropylpyrazino[2,3-c]-1,2,6-thiadiazine 2,2-dioxide.

4-amino-1,6-diethyl-7-methylpyrazino[2,3-c]-1,2,6-thiadiazine 2,2-dioxide.

4-amino-1-ethyl-6,7-diphenylpyrazino[2,3-c]-1,2,6-thiadiazine 2,2-dioxide.

1,7-diethyl-4-hydrazino-pyrazino[2,3-c]-1,2,6-thiadiazine 2,2-dioxide.

These compounds of the present invention, structurally related to the pteridines, have interesting properties as diuretics, bronchodilators and platelet antiaggregants.

In this respect, it is noted that Spanish patent 531.160 teaches 4-amino and 4-oxo-8H-pyrazino[2,3-c] [1,2,6]-thiadiazine 2,2-dioxides and the 6,7-disubstituted derivatives thereof, of general formula

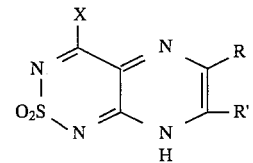

where:

R and R' are hydrogen, straight or branched chain alkyl radicals, aryl, aralkyl, cycloalkyl or other appropriate substituent; and X is an animo or hydroxyl group.

These compounds may be considered to be pteridine 2S-ioxo isosteres, compounds of indubitable biological importance, since, apart from forming part of many natural pigments, some of the derivatives thereof are intermediates in the biosynthesis of riboflavins and are present as cofactors in certain enzymes.

The compounds of the present invention, as said above, are N-substituted, which is an important item of differentiation over those of Spanish patent 531.160, which are not N-substituted, as may be seen.

The invention relates also to a process for the preparation of the compounds cited in the title.

This process is characterized in that it comprises the following steps: 1) condensation of o-diaminothiadiazine of formula II

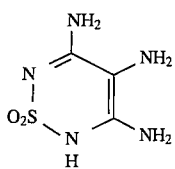

with 1,2-dicarbonyl compounds or α-hydroxyiminoketones of formula III

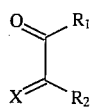

where $R_1$ and $R_2$ have the meaning given above and X is oxygen or hydroxyimino, to give a compound of formula IV

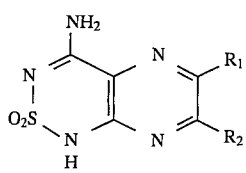

where $R_1$ and $R_2$ have the meaning given above in I; and 2) alkylation of the compounds of formula IV, to obtain a compound of formula V

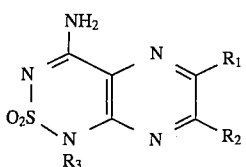

According to the invention, this formula V compound is alternatively alkylated or transaminated, to give the compound of formula I.

The compound of formula V is preferably alkylated by dissolving it (preferably in acetone) and reacting it with an alkyl halogen.

In the case of transamination, it is preferably carried out by dissolving the compound of formula V (preferably in an alcohol) and reacting it with an amine.

The step 2) alkylation may be carried out in several ways. The invention contemplates preferably the cases described below.

In the first place the compound of formula IV is dissolved and reacted with an alkyl sulphate. The solvent is preferably an aqueous potassium carbonate solution.

The alkylation may also be carried out by dissolving the compound of formula IV (preferably in acetone) and reacting it with an alkyl halide and potassium carbonate under reflux.

A third way of carrying out the step 2) alkylation is to treat the compound of formula IV with hexamethyldisilazane, to obtain a silylated derivative which is reacted with an alkyl halide.

Preferably, the hexamethyldisilazane treatment is carried out under reflux, in the presence of a catalyst (such as ammonium sulphate or trimethylsilyl chloride) under an inert gas atmosphere (such as nitrogen or argon).

The invention finally contemplates the possibility of carrying out the step 2) alkylation by treating the compound of formula IV with N-(2-chloroethyl)-N,N-dialkylammonium chloride under phase transfer conditions with tetrabutylammonium bromide, in an aqueous potassium carbonate and methylene chloride or 1,2-dichloroethane solution.

Where $R_1$ is bromine in the formula IV compounds, these are prepared by treating a corresponding formula IV compound where $R_1$ is hydrogen with N-bromosuccinimide in methanol.

The formula IV compounds preferably used are:

4-amino-6,7-dimethyl-1H-pyrazino[2,3-c]-1,2,6-thiadiazine 2,2-dioxide;

4-amino-6-methyl-7-ethyl-1H-pyrazino[2,3-c]-1,2,6-thiadiazine 2,2-dioxide, prepared by condensation of o-diaminothiadiazine with 2,3-pentanedione;

4-amino-6,7-diethyl-1H-pyrazino[2,3-c]-1,2,6-thiadiazine 2,2-dioxide, prepared by condensation of o-diaminothiadiazine with 3,4-hexanedione;

4-amino-6,7-bis(trifluoromethyl)-1H-pyrazino[2,3-c]-1,2,6-thiadiazine 2,2-dioxide, prepared by condensation of o-diaminothiadiazine with 1,1,1,4,4,4-hexafluoro-2,3-butanedione;

4-amino-6,7,8,9-tetrahydro-1H-pyrazino-1,2,6-thiadiazine[3,4-b]quinoxaline 2,2-dioxide, prepared by condensation of o-diaminothiadiazine with 1,2-cyclohexanedione;

4-amino-6-phenyl-7-methyl-1H-pyrazino[2,3-c]-1,2,6-thiadiazine 2,2-dioxide, prepared by condensation of o-diaminothiadiazine with α-hydroxyiminoacetophenone;

4-amino-6-methyl-7-propyl-1H-pyrazino[2,3-c]-1,2,6-thiadiazine 2,2-dioxide, prepared by condensation of o-diaminothiadiazine with 2,3-hexanedione;

4-amino-6,7-diisopropyl-1H-pyrazino[2,3-c]-1,2,6-thiadiazine 2,2-dioxide, prepared by condensation of o-diaminothiadiazine with diisobutyryl;

4-amino-6-ethyl-7-methyl-1H-pyrazino[2,3-c]-1,2,6-thiadiazine 2,2-dioxide, prepared by condensation of o-diaminothiadiazine with 2-(hydroxyimino)-3-pentanone;

4-amino-6-methyl-1H-pyrazino[2,3-c]-1,2,6-thiadiazine 2,2-dioxide, prepared by condensation of o-diaminothiadiazine with 1-pyruvaldoxime.

4-amino-7-methyl-1H-pyrazino[2,3-c]-1,2,6-thiadiazine 2,2-dioxide.

4-amino-6-phenyl-1H-pyrazino[2,3-c]-1,2,6-thiadiazine 2,2-dioxide.

4-amino-7-phenyl-1H-pyrazino[2,3-c]-1,2,6-thiadiazine 2,2-dioxide.

4-amino-6-bromo-7-phenyl-1H-pyrazino[2,3-c]-1,2,6-thiadiazine 2,2-dioxide.

4-amino-6-bromo-7-methyl-1H-pyrazino[2,3-c]-1,2,6-thiadiazine 2,2-dioxide.

The synthesized products have been subjected to a general pharmacological screening, by application of a broad range of biological assays, to bring to light potential activities of therapeutic interest. Outstanding among the results obtained are the diuretic, bronchodilatory and platelet antiaggregation activities for a certain number of the compounds tested, which activities were valued at greater depth.

The synthesized compounds were, therefore, subjected a pharmacological screening to evaluate a possible diuretic and salt excreting activity. Thus, an acute dose of each of the products of synthesis (20 or 25 mg/kg) was administered to rats and the amount of urine and the excretion of electrolytes was measured, following the technique described by Lipschits et al., with certain modifications (J. Pharmacol. Exp.Ther. 1943–79; 97–110).

The volume (ml/kg/6 h), the pH and the excretion of sodium, potassium and chloride ions (mEq/kg/6 h) were determined on the urine quantitatively collected over 6 hours, using triamterene and hydrochlorothiazide as reference diuretics.

Likewise, to complete the superficial pharmacological profile, a check was made of the mortality rate in the mouse after oral administration of a single dose of 1600 mg/kg of each of the synthesized compounds (See Table 1).

TABLE 1

DIURETIC AND SALURETIC ACTIVITY OF THE SYNTHESIZED COMPOUNDS, SUMMARY OF THE PHARMACOLOGICAL SCREENING TESTS.
Activity expressed as treated group/control group ratio.

| Compound | Doses (mg/kg, po) | Volume urine | Na | K | Cl | Na/K | Mortality (%) at 1600 mg/kg po |
|---|---|---|---|---|---|---|---|
| REFERENCES | | | | | | | |
| Triamterene | 20 | 1.45 | 5.79 | 0.34 | 2.37 | 17.03 | — |
| Triamterene | 25 | 1.65 | 5.96 | 0.36 | 2.60 | 16.56 | — |
| Hydrochlorothiazide | 10 | 1.66 | 6.68 | 2.17 | 5.77 | 3.08 | — |
| Hydrochlorothiazide | 40 | 1.79 | 7.73 | 2.65 | 6.26 | 2.92 | — |
| 4-aminopyrazino[2,3-c]-1,2,6-thiadiazine | | | | | | | |
| 1-[2-(N,N-diisopropyl-amino)ethyl]-6,7-dimethyl | 25 | 0.84(N) | 1.93 | 0.94(N) | 1.56 | 2.05 | 62% |
| 1-(2-morpholinoethyl)-6,7-dimethyl | 25 | 1.08(N) | 2.46(N) | 1.12(N) | 1.02(N) | 2.20 | 85% |
| 1,7-diethyl-6-methyl | 25 | 1.97 | 8.23 | 1.79 | 7.87 | 4.60 | 37.5% |
| 1-(2-hydroxyethyl)-6,7-dimethyl | 25 | 1.06(N) | 2.03 | 1.89(N) | 1.41(N) | 1.07 | 0% |
| 1-ethyl-6,7-bis(trifluoromethyl) | 25 | 1.28 | 1.29(N) | 0.99(N) | 1.12(N) | 1.30 | 100% |
| 1-ethyl-7-phenyl | 20 | 1.21 | 1.31 | 1.40 | 1.36(N) | 0.94 | — |
| 6,7-dimethyl-1-propyl | 20 | 1.75 | 6.09 | 1.97 | 5.93 | 3.09 | 60% |
| 4-aminopyrazino[2,3-c]-1,2,6-thiadiazine | | | | | | | |
| 1-ethyl-6-phenyl-7-methyl | 20 | 1.21 | 1.42(N) | 0.85(N) | 1.23(N) | 1.65 | — |
| 1,6,7-triethyl | 20 | 1.33 | 1.98 | 1.27(N) | 2.16(N) | 1.56 | 50% |
| 1-ethyl-6-methyl-7-propyl | 20 | 1.09(N) | 1.56 | 1.23(N) | 1.76(N) | 1.27 | 50% |
| 1-ethyl-6-methyl-1-propyl | 20 | 1.54 | 5.02 | 1.72 | 5.30 | 2.92 | 40% |
| 7-ethyl-1,6-dimethyl | 20 | 1.52 | 3.85 | 1.77 | 4.71 | 2.18 | 0% |
| 1,6-diethyl-7-methyl | 20 | 1.04(N) | 0.56(N) | 0.91(N) | 0.89(N) | 0.62(N) | — |
| 1,7-diethyl-4-(methyl-amino)-6-methyl | 20 | 1.39 | 3.44 | 1.55 | 4.24 | 1.56 | — |

(N): Indicates that the difference relative to the control group is not statistically significant.

The compounds of the present invention have a bronchodilatory action. This activity has been evidenced in "in vitro" tests through the capacity of reducing the spontaneous tone in isolated guinea pig trachea preparations, according to the method of Luduena, F. P. et al. (Arch. Int. Pharmacodyn. 111; 392–400, 1957) (See Table 2).

TABLE 2

Trachea relaxing activity of the synthesized products. Summary of the "in vitro" pharmacological screening tests.

| Compound | concentration (mcg/ml) | Trachea relaxing activity (%) |
|---|---|---|
| REFERENCE | | |
| Theophylline | 30 | 60 |
| Amrinone | 3 | 65 |
| 4-aminopyrazino[2,3-c]-1,2,6-thiadiazine | | |
| 4-amino-1-ethyl-6,7,8,9-tetrahydro-1,2,6-thiadiazino[3,4-b]quinoxaline | 30 | 82 |
| 1-[(2-ethoxycarbonyl)-methyl]-7-phenyl | 30 | 72 |
| 1-ethyl-7-phenyl | 30 | 95 |
| 1-ethyl-6-phenyl-7-methyl | 30 | 93 |
| 6-bromo-1-ethyl-7-phenyl | 30 | 63 |
| 6-bromo-1-ethyl-7-methyl | 30 | 88 |
| 1-ethyl-6-methyl | 30 | 67 |
| 7-ethyl-1,6-dimethyl | 30 | 95 |
| 1,6-diethyl-7-methyl | 30 | 95 |
| 1,7-diethyl-4-(methylamino)-6-methyl | 30 | 75 |
| 1,7-diethyl-4-hydrazino | 30 | 72 |

The compounds of the present invention have also shown a remarkable bronchodilatory effect "in vivo". Konzett and Rosslet's technique was used for evaluation, with the capacity of the tested products, when administered intraduodenally at dose levels of 25 and 100 mg/kg, to antagonize a histamine induced bronchospasm (7.5 mcg/ml) in anaesthetized guinea pig being determined. Theophylline (25 mg/kg, i.d.) was used as reference drug, with the areas under the curve defined by the bronchospasm inhibition percentages and the post-administration time being compared. Some of the products tested showed an "in vivo" bronchodilatory activity comparable with or superior to that of theophylline and may, therefore, be useful as antiasthma and bronchodilatory drugs (See Table 3).

TABLE 3

Bronchodilatory effect in vivo according to the method of Konzett and Rossler, antagonizing the histamine induced bronchospasm.

| Compound | Bronchodilatory activity (area ratio) |
| --- | --- |
| REFERENCE | |
| Theophylline | 25 mg/kg i.d.:1 |
| | 100 mg/kg i.d.:1 |
| 4-aminopyrazino[2,3-c]-1,2,6-thiadiazine | |
| 4-amino-1-ethyl-6,7,8,9-tetrahydro-1,2,6-thiadiazino[3,4-b]quinoxaline | 25 mg/kg i.d.:0.6 |
| | 100 mg/kg i.d.:0.4 |
| 1-ethyl-6-methyl | 25 mg/kg i.d.:0.8 |
| | 100 mg/kg i.d.:1.3 |

The platelet antiaggregation activity was determined in vitro using platelet rich rabbit plasma and arachidonic acid (50 mcg/ml) as aggregation inducing agent. The results obtained in the evaluation of both effects are summarized in Table 4. The results are given for tracheal relaxation as percentage inhibition of the tracheal tone relative to the maximum relaxation induced by noradrenaline (0.3 mcg/ml) and for the platelet aggregation as a percentage of the maximum effect observed with the proaggregation agent.

TABLE 4

Platelet antiaggregation activity of the synthesized products. Summary of in vitro pharmacological screening

| Compound | Concentration (mcg/ml) | platelet antiaggregation activity (%) |
| --- | --- | --- |
| REFERENCE | | |
| Aspirin | 2.5 | 100 |
| 4-aminopyrazino[2,3-c]-1,2,6-thiadiazine | | |
| 1-ethyl-6-phenyl | 10 | 100 |
| 1-ethyl-6-phenyl-7-methyl | 10 | 100 |
| 6-bromo-1-ethyl-7-phenyl | 10 | 100 |
| 1-ethyl-6,7-diphenyl | 10 | 100 |

The platelet antiaggregation activity of the active products in the initial screening (Table 4) has been confirmed and extended by evaluating the capacity thereof to inhibit in vitro the aggregation of human platelets using Born's method. ADP (1 mcM), collagen (2 mcg/ml), arachidonic acid (1 mM), U-46619 (1,4 mcM) and IBOP (225 nM) were used as aggregation inducing agents. The results obtained (Table 5) show the capacity of the products tested to inhibit dose dependently the platelet aggregation induced by collagen, arachidonic acid, U-46619 and IBOP, probably through interaction with the platelet endoperoxide/thromboxane receptor. Therefore, said compounds might be potentially useful in the treatment of disorders in which the thromboxanes play a part, such as myocardial infarct, cerebrovascular diseases and asthmatic and/or inflammatory states.

TABLE 5

Concentrations in mcM of the products tested inhibiting > 60% platelet aggregation induced by different agents.

| | Inducing agent | | | |
| --- | --- | --- | --- | --- |
| Compound | Collagen | Arachidonic acid | U-46619 | IBOP |
| BAY-U | 0.2 | 0.2 | 0.2 | 0.1 |
| 4-aminopyrazino[2,3-c]-1,2,6-thiadiazine | | | | |
| 1-ethyl-6-phenyl | 1 | 30 | 10 | 1 |
| 1-ethyl-6-phenyl-7-methyl | 1 | 30 | 3 | 3 |
| 1-ethyl-6,7-diphenyl | 1 | 30 | 1 | 3 |

The compounds of this invention may be used as drugs in human therapy. They may be administered as pharmaceutical compositions in combination with pharmacologically acceptable excipients or vehicles, for example as tablets, coated tablets, sustained release tablets, capsules, syrups and suppositories. In the case of soluble salts, they may be administered as injectables.

Examples are given hereinafter to illustrate the said process, without them being considered as limitations of the invention.

EXAMPLE 1

(Representative Method A)

Preparation of 4-amino-1-ethyl-6,7-dimethylpyrazino[2,3-c]-1,2,6,thiadiazine 2,2-dioxide (I, $R_1$=Me, $R_2$=Me, $R_3$=Et, $R_4$ and $R_5$=H)

3 ml of diethyl sulphate were added to a solution of 1 g (4.4 mmoles) of 4-amino-6,7-dimethyl-1H-pyrazino[2,3-c]-1,2,6-thiadiazine 2,2-dioxide in 25 ml of water and 2 g of potassium carbonate. The solution was stirred at room temperature for twelve hours and the precipitated solid was recrystallized from water-ethanol, to give the desired product. See Table 6.

EXAMPLE 2

(Representative Method B)

Preparation of 4-amino-1-ethyl-6-phenylpyrazino[2,3-c]-1,2,6-thiadiazine 2,2-dioxide (I, $R_1$=Ph, $R_2$=H, $R_3$=Et, $R_4$ and $R_5$=H)

A solution of 1 g (3,6 mmoles) of 4-amino-6-phenyl-1H-pyrazino[2,3-c]-1,2,6-thiadiazine 2,2-dioxide in 140 ml of acetone and 0.25 g (1.8 mmoles) of potassium carbonate was treated with 2 ml of ethyl iodide under reflux for 6 hours. The acetone was removed under vacuum and water was added. A solid precipitated out and was recrystallized from water/methanol, to give the desired compound. See Table 6.

EXAMPLE 3

(Representative Method C)

Preparation of
4-amino-1-[(2-ethoxycarbonyl)methyl]-6,7-
dimethylpyrazino[2,3-c]-1,2,6-thiadiazine
2,2-dioxide ($R_1$=Me, $R_2$=Me, $R_3$=$CH_2$—$CO_2$Et, $R_4$
and $R_5$=H).

3 g (10.8 mmoles) of 4-amino-6,7-dimethyl-1H-pyrazino [2,3-c]-1,2,6-thiadiazine 2,2-dioxide were reacted with 50 ml of hexamethyldisilazane, in the presence of catalytic amounts of ammonium chloride, under a nitrogen atmosphere. The solution was dried and the residue was treated with 3 ml of ethyl bromoacetate in 20 ml of methylene chloride under reflux for 6 hours. Subsequently, the solvent was removed under vacuum and the residue was recrystallized from water/methanol, to give the desired product. See Table 6.

EXAMPLE 4

(Representative Method D)

Preparation of 4-amino-1-(2-morpholinoethyl)-6,7-
dimethylpyrazino[2,3-c]-1,2,6-thiadiazine
2,2-dioxide ($R_1$=Me, $R_2$=Me, $R_3$=$OH_2$—$OH_2$—N
O, $R_4$ and $R_5$=H)

1.4 g (6.2 mmoles) of 4-amino-6,7-dimethyl-1H-pyrazino [2,3-c]-1,2,6-thiadiazine 2,2-dioxide were reacted with 1.2 g (6.5 mmoles) of 4-(2-chloroethyl) hydrochloride/morpholine in 50 ml of water, 75 ml of methylene chloride, 5 g of potassium carbonate and 0.3 g of tetrabutylammonium bromide. The mixture was stirred at room temperature for 12 hours and the organic phase was extracted and after being evaporated to dryness, the residue was recrystallized from water/methanol to give the desired product. See Table 6.

EXAMPLE 5

(Representative method E)

1,7-diethyl-4-(methylamino)-6-methylpyrazino
[2,3-c]-1,2,6-thiadiazine 2,2-dioxide (I, $R_1$=Me,
$R_2$=Et, $R_3$=Et, $R_4$=H and $R_5$=Me)

A solution of 1 g (3,7 mmoles) of 4-amino-1,7-diethyl-6-methylpyrazino[2,3-c]-1,2,6-thiadiazine 2,2-dioxide in acetone and 0.26 g (1.85 mmoles) of potassium carbonate was treated with an excess of methyl iodide, under reflux for 8 hours. The acetone was removed under vacuum and water was added, to precipitate a solid which was purified by column chromatography using chloroform/methanol (50:1) as eluent.

EXAMPLE 6

(Representative Method F)

Preparation of
1,7-diethyl-4-(2-hydroxyethylamino)-6-methylpyrazino
[2,3-c]-1,2,6-thiadiazine 2,2-dioxide (I, $R_1$=Me,
$R_2$=Et, $R_3$=Et, $R_4$=H and $R_5$=$CH_2CH_2OH$)

A solution of 1.5 g (5.58 mmoles) of 4-amino-1,7-diethyl-6-methylpyrazino[2,3-c]-1,2,6-thiadiazine 2,2-dioxide in 50 ml of methanol was treated with 3.4 g (55.8 mmoles) of ethanolamine under reflux for 28 hours. The methanol was removed under vacuum, water was added and the precipitated solid was purified by recrystallization from water/methanol. See Table 6.

EXAMPLES 7–28

The products listed in Table 6 were obtained using the experimental conditions described under Examples 1–5, as indicated in each case.

EXAMPLE A

Preparation of the Galenic Form of Tablets (1) Composition:

| | |
|---|---|
| 4-amino-1,7-diethyl-6-methylpyrazino [2,3-c]-1,2,6-thiadiazine 2,2-dioxide | 50 mg |
| Avicel pH 102 SCG | 50 mg |
| Starch 1,500 | 25 mg |
| Talc | 10 mg |
| Precirol ATO 5 | 2 mg |

(2) Preparation

The 4-amino-1,7-diethyl-6-methylpyrazino[2,3-c]-1,2,6-thiadiazine 2,2-dioxide, Avicel pH 102 SCG and Starch 1,500 were blended for 25 minutes after having been previously sifted through a 0.5 mm diameter mesh sieve.

The talc and the Precirol ATO 5, previously sifted for 5–10 minutes through a 0.5 mm mesh sieve, were added.

The mixture was compressed in a rotary machine to a theoretical weight of 137 mg with a double concave 8 mm diameter punch.

EXAMPLE B

Preparation of the Galenic Form of Retard Tablets (1) Composition

| | |
|---|---|
| 4-amino-1-ethyl-6-methylpyrazino [2,3-c]-1,2,6-thiadiazine 2,2-dioxide | 300 mg |
| Ground sugar | 60 mg |
| Plasdone | 20 mg |
| Talc | 5 mg |
| Precirol ATO 5 | 15 mg |

(2) Preparation

The 4-amino-1-ethyl-6-methylpyrazino[2,3-c]-1,2,6-thiadiazine 2,2-dioxide and the ground sugar were blended for 25 minutes after having been previously sifted through a 0.5 mm diameter mesh sieve.

A hydroalcoholic suspension of plasdone and Precirol ATO 5 was added to the resulting blend, with kneading until an appropriate consistency was obtained. Granules were formed through a 3 mm diameter sieve and were dried in a fluid bed at 60° C. The granules were ground, sifted through a 0.7 mm mesh sieve and blended with the talc.

The mixture was compressed in a rotary machine to a theoretical weight of 400 mg with double concave 10 mm diameter punches.

EXAMPLE C

Preparation of the Galenic Form of Capsules

(1) Composition:

| | |
|---|---|
| 4-amino-1-ethyl-6-phenylpyrazino [2,3-c]-1,2,6-thiadiazine 2,2-dioxide | 50 mg |
| Lactose | 50 mg |
| Magnesium stearate | 5 mg |

(2) Preparation

The 4-amino-1-ethyl-6-phenylpyrazino[2,3-c]-1,2,6-thiadiazine 2,2-dioxide and lactose were blended for 25 minutes after having been previously sifted through a 0.5 mm diameter mesh sieve.

The magnesium stearate, previously sifted through a 0.5 mm mesh sieve, was added and blending was continued for 5–10 minutes.

Hard gelatine capsules with a theoretical content of 105 mg each were filled.

TABLE 6

LIST OF THE SYNTHESIZED N(1) SUBSTITUTED PYRAZINO [2,3-c]-1,2,6-THIADIAZINE 2,2-DIOXIDES
Synthesis and analytical characteristics

| Ex. N° | 4-aminopyrazino[2,3-c]-1,2,6-thiadiazine | Method | $R_1$ | $R_2$ | $R_3$ | $R_4$ | $R_5$ | m.p. (°) | | Elementary analysis (%) C | H | N | S |
|---|---|---|---|---|---|---|---|---|---|---|---|---|---|
| 1 | 1-ethyl-6,7-dimethyl | A | Me | Me | Et | H | H | 167–169[a] | C F | 42.34 42.00 | 5.13 5.21 | 27.43 27.30 | 12.56 12.49 |
| 2 | 1-ethyl-6-phenyl | B | Ph | H | Et | H | H | 265–267[b] | C F | 51.47 51.51 | 4.32 4.40 | 23.09 22.29 | 10.57 10.68 |
| 3 | 1-[(etoxycarbonyl)methyl]-6,7-dimethyl | C | Me | Me | $CH_2CO_2Et$ | H | H | 186–188[a] | C F | 42.17 42.38 | 4.83 5.12 | 22.35 22.48 | 10.23 10.60 |
| 4 | 1-(2-morpholinoethyl)-6,7-dimethyl | D | Me | Me | $CH_2CH_2N\quad O$ | H | H | 260–262[a] | C F | 45.87 45.75 | 5.92 6.07 | 24.69 24.65 | 9.42 9.80 |
| 5 | 1,7-diethyl-4-(methyl-amino)-6-methyl | E | Me | Et | Et | H | Me | 164–166[b] | C F | 46.63 46.42 | 6.05 5.90 | 24.72 24.60 | |
| 6 | 1,7-diethyl-4-(2-hydroxy-ethylamino)-6-methyl | F | Me | Et | Et | H | $CH_2CH_2OH$ | 181–182[a] | C F | 45.94 46.02 | 6.11 5.96 | 22.35 22.60 | 10.23 10.50 |
| 7 | 1-[2-(N,N-dimethyl-amino)ethyl]-6,7-dimethyl | D | Me | Me | $CH_2-CH_2N(CH_3)_2$ | H | H | 218–220[a] | C F | 44.28 44.11 | 6.08 6.27 | 28.17 27.89 | 10.75 11.08 |
| 8 | 1-[2-(N,N-diisopropyl-amino)ethyl]-6,7-dimethyl | D | Me | Me | $CH_2-CH_2N^iPr_2$ | H | H | 161–162[a] | C F | 50.83 50.90 | 7.39 7.50 | 23.71 23.50 | 9.05 9.14 |
| 9 | 1,7-diethyl-6-methyl | A | Me | Et | Et | H | H | 194–196[a] | C F | 44.60 44.32 | 5.61 5.63 | 26.00 26.02 | 11.91 11.66 |
| 10 | 1-[(etoxycarbonyl)methyl]-7-phenyl | B | H | Ph | $CH_2-CO_2Et$ | H | H | 190–192[a] | c F | 47.61 47.46 | 4.26 4.55 | 18.51 18.30 | |
| 11 | 1-(2-hydroxyethyl)-6,7-dimethyl | A | Me | Me | $CH_2CH_2OH$ | H | H | 171–172[a] | C F | 39.85 40.00 | 4.83 4.59 | 25.81 26.12 | 11.82 11.75 |
| 12 | 1-ethyl-6,7-bis(trifluoromethyl) | A | $CF_3$ | $CF_3$ | Et | H | H | 217–219[a] | C F | 29.76 29.86 | 1.94 2.18 | 19.28 19.33 | 8.83 8.74 |
| 13 | 1-ethyl-7-phenyl | A | H | Ph | Et | H | H | 246–248[b] | C F | 51.47 51.67 | 4.32 4.46 | 23.09 22.89 | 10.57 10.20 |
| 14 | 6,7-dimethyl-1-propyl | C | Me | Me | Pr | H | H | 165–167[a] | C F | 44.60 44.70 | 5.61 5.77 | 26.00 25.74 | 11.90 11.70 |
| 15 | 6-bromo-1-ethyl-7-phenyl | A | Br | Ph | Et | H | H | 234–236[a] | C F | 40.85 41.00 | 3.16 3.24 | 18.32 18.35 | 8.39 8.11 |
| 16 | 1,6,7-triethyl | A | Et | Et | Et | H | H | 190–191[a] | C F | 46.63 46.67 | 6.05 6.19 | 24.72 24.50 | 11.32 10.99 |
| 17 | 4-amino-1-ethyl-6,7,8,9-tetrahidro-1,2,6-thiadiazino[3,4-b]quinoxaline | A | $(CH_2)2-(CH_2)2$ | | Et | H | H | 198–200[a] | C F | 46.96 46.96 | 5.37 5.11 | 24.89 24.52 | 11.40 |
| 18 | 1-ethyl-6-phenyl-7-methyl | A | Ph | Me | Et | H | H | 161–163[a] | C F | 52.98 53.03 | 4.76 4.93 | 22.07 21.90 | 10.10 9.81 |
| 19 | 1-ethyl-6-methyl | B | Me | H | Et | H | H | 171–173[a] | C F | 39.83 39.74 | 4.59 4.62 | 29.03 29.18 | 13.29 12.98 |
| 20 | 6-bromo-1-ethyl-7-methyl | A | Br | Me | Et | H | H | 172–174[b] | C F | 30.01 29.89 | 3.15 3.48 | 21.87 21.70 | 10.01 10.08 |
| 21 | 1-ethyl-7-phenyl | A | H | Me | Et | H | H | 202–204[b] | C F | 39.83 39.93 | 4.59 4.80 | 29.03 28.71 | |
| 22 | 1-ethyl-6-methyl-7-propyl | A | Me | Pr | Et | H | H | 142–144[b] | C F | 46.63 46.50 | 6.05 5.75 | 24.72 24.42 | |
| 23 | 7-ethyl-6-methyl-1-propyl | A | Me | Et | Pr | H | H | 158–160[b] | C F | 46.63 46.34 | 6.05 5.92 | 24.72 24.50 | |
| 24 | 7-ethyl-1,6-dimethyl | A | Me | Et | Me | H | H | 240–242[b] | C F | 42.34 42.70 | 5.13 5.01 | 27.43 27.20 | 12.56 12.33 |
| 25 | 1-ethyl-6,7-diisopropyl | A | Pr | Pr | Et | H | H | 157–158[b] | C F | 50.14 49.80 | 6.80 6.72 | 22.49 22.27 | 10.30 10.45 |
| 26 | 1,6-diethyl-7-methyl | A | Et | Me | Et | H | H | 145–146[b] | C F | 44.60 44.73 | 5.61 5.33 | 26.00 25.90 | 11.91 |
| 27 | 1-ethyl-6,7-diphenyl | B | Ph | Ph | Et | H | H | 325– | C | 60.14 | 4.52 | 18.46 | |

TABLE 6-continued

LIST OF THE SYNTHESIZED N(1) SUBSTITUTED PYRAZINO [2,3-c]-1,2,6-THIADIAZINE 2,2-DIOXIDES
Synthesis and analytical characteristics

| Ex. N° | 4-aminopyrazino[2,3-c]-1,2,6-thiadiazine | Method | $R_1$ | $R_2$ | $R_3$ | $R_4$ | $R_5$ | m.p. (°) | Elementary analysis (%) | | | |
|---|---|---|---|---|---|---|---|---|---|---|---|---|
| | | | | | | | | | C | H | N | S |
| 28 | 1,7-diethyl-4-hydrazino | F | Me | Et | Et | H | $NH_2$ | 327[a] 170– 172[a] | F 60.44 C 42.24 F 42.50 | 4.82 5.67 5.96 | 18.77 29.56 29.40 | 11.28 11.01 |

[a]Recrystallized from water/ethanol.
[b]Recrystallized from water/methanol.

We claim:

1. A 1N substituted pyrazino [2,3-c]-1,2,6-thiadiazine 2,2-dioxides of formula I:

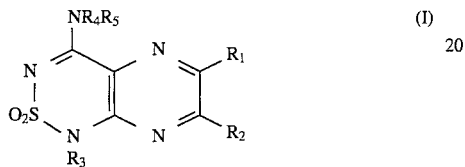

wherein $R_1$ and $R_2$ are the same or different;

such that when $R_1$ and $R_2$ are different, $R_1$ and $R_2$ are selected from the group consisting of hydrogen, straight or branched chain $C_1$–$C_5$ alkyl, trifluoromethyl, halogen, amino, carboxamido, $C_1$–$C_5$ alkoxycarbonyl, phenyl, and substituted phenyl, said substituted phenyl containing from one to three substituents selected from halogen, hydroxy, amino, methyl, methoxy, nitro and N-mono or dimethylamino, and $R_3$ is selected from the group consisting of straight or branched chain $C_1$–$C_5$ alkyl, di($C_1$–$C_5$)alkylaminoethyl, hydroxyethyl, $C_1$–$C_5$)alkoxycarbonylmethyl, carboxymethyl, morpholinoethyl, benzyl and substituted benzyl, said substituted benzyl containing a phenyl group containing 1, 2 or 3 substituents, said substituents being selected from the group consisting of halogen, hydroxy, methyl, methoxy, nitro and N-mono or dimethylamino;

such that when $R_1$ and $R_2$ are the same, $R_1$ and $R_2$ are selected from the group consisting of hydrogen, straight or branched chain $C_1$–$C_5$ alkyl, trifluoromethyl, phenyl, and substituted phenyl, said substituted phenyl containing from one to three substituents selected from halogen, hydroxy, amino, methyl, methoxy, nitro and N-mono or dimethylamino, and $R_3$ is selected from the group consisting of ethyl, propyl, butyl, di($C_1$–$C_5$)alkylaminoethyl, hydroxyethyl, ($C_1$–$C_5$)alkoxycarbonylmethyl, carboxymethyl, morpholinoethyl, benzyl and substituted benzyl, said substituted benzyl containing a phenyl group containing 1, 2 or 3 substituents, said substituents being selected from the group consisting of halogen, hydroxy, methyl, methoxy, nitro and N-monomethylamino or dimethylamino;

with the proviso that when $R_1$ and $R_2$ are the same and $R_3$ is methyl, then $R_1$ and $R_2$ are selected from the group consisting of hydrogen, ethyl, propyl, isopropyl, sec-butyl, tert-butyl, trifluoromethyl and substituted phenyl; said substituted phenyl containing 1, 2 or 3 substituents, wherein when said substituted phenyl contains only one substituent, said substituent is selected from the group consisting of fluoro, bromo, hydroxy, amino, methyl, nitro, and N-mono or dimethylamino, and wherein when said substituted phenyl contains two or three substituents, said substituents are selected from the group consisting of halogen, amino, methyl, methoxy, nitro, N-monomethylamino or N-dimethylamino;

and $R_4$ and $R_5$ are the same or different and are selected from the group consisting of hydrogen, straight or branch chain $C_1$–$C_5$ alkyl, hydroxy $C_1$–$C_5$alkyl, amino, amino$C_1$–$C_5$alkyl, $C_1$–$C_5$alkyl-amino$C_1$–$C_5$alkyl;

except that when $R_4$ and $R_5$ are different and are selected from the group consisting of hydrogen and amino, then R3 is not ethyl and R1 and R2 are not both phenyl or methyl.

2. A pharmaceutical composition having diruetic, bronchodilator or platelet antiaggregation activity comprising:

a) as an active ingredient a therapeutically effective amount of a 1N substituted pyrazino [2,3-c]-1,2,6-thiadiazine 2,2-dioxides of formula I:

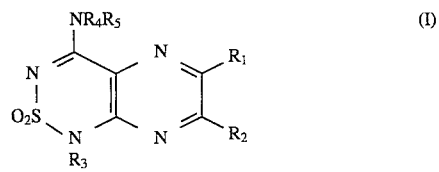

wherein $R_1$ and $R_2$ are the same or different;

such that when $R_1$ and $R_2$ are different, $R_1$ and $R_2$ are selected from the group consisting of hydrogen, straight or branched chain $C_1$–$C_5$ alkyl, trifluoromethyl, halogen, amino, carboxamido, $C_1$–$C_5$ alkoxycarbonyl, phenyl, and substituted phenyl, said substituted phenyl containing from one to three substituents selected from halogen, hydroxy, amino, methyl, methoxy, nitro and N-mono or dimethylamino, and $R_3$ is selected from the group consisting of straight or branched chain $C_1$–$C_5$ alkyl, di($C_1$–$C_5$)alkylaminoethyl, hydroxyethyl, $C_1$–$C_5$)alkoxycarbonylmethyl, carboxymethyl, morpholinoethyl, benzyl and substituted benzyl, said substituted benzyl containing a phenyl group containing 1, 2 or 3 substituents, said substituents being selected from the group consisting of halogen, hydroxy, methyl, methoxy, nitro and N-mono or dimethylamino;

such that when $R_1$ and $R_2$ are the same, $R_1$ and $R_2$ are selected from the group consisting of hydrogen, straight or branched chain $C_1$–$C_5$ alkyl, trifluoromethyl, phenyl, and substituted phenyl, said substituted phenyl containing from one to three substituents selected from halogen, hydroxy, amino, methyl, methoxy, nitro and N-mono or dimethylamino, and $R_3$ is selected from the group consisting of ethyl, propyl, butyl, di($C_1$–$C_5$)alkylaminoethyl, hydroxyethyl, ($C_1$–$C_5$)alkoxycarbonylmethyl, carboxymethyl, morpholinoethyl, benzyl and substituted benzyl, said substituted benzyl containing a phenyl group containing 1, 2 or 3 substituents, said substituents being selected from the group consisting of halogen, hydroxy, methyl, methoxy, nitro and N-monomethylamino or dimethylamino;

with the proviso that when $R_1$ and $R_2$ are the same and $R_3$ is methyl, then $R_1$ and $R_2$ are selected from the group consisting of hydrogen, ethyl, propyl, isopropyl, sec-butyl, tert-butyl, trifluoromethyl and substituted phenyl, said substituted phenyl containing 1, 2 or 3 substituents, wherein when said substituted phenyl contains only one substituent, said substituent is selected from the group consisting of fluoro, bromo, hydroxy, amino, methyl, nitro, and N-mono or dimethylamino, and wherein when said substituted phenyl contains two or three substituents, said substituents are selected from the group consisting of halogen, amino, methyl, methoxy, nitro, N-monomethylamino or N-dimethylamino;

and $R_4$ and $R_5$ are the same or different and are selected from the group consisting of hydrogen, straight or branch chain $C_1$–$C_5$ alkyl, hydroxy $C_1$–$C_5$ alkyl, amino, amino$C_1$–$C_5$alkyl, $C_1$–$C_5$alkyl-amino$C_1$–$C_5$alkyl; and b) one or more pharmaceutically acceptable excipients.

3. The composition of claim 2 wherein said 1N substituted pyrazino[2,3-c]-1,2,6-thiadiazine 2,2-dioxide has the chemical name:

4-amino-1-ethyl-6-phenylpyrazino[2,3-c]-1,2,6-thiadiazine 2,2-dioxide, 4-amino-6,7-dimethylpyrazino[2,3-c]-1,2,6-thiadiazine 1-[(ethoxycarbonyl)methyl] 2,2-dioxide, 4-amino-6,7-dimethyl-1-(2-morpholinoethyl)-pyrazino[2,3-c]-1,2,6-thiadiazine 2,2-dioxide 4-(2-hydroxyethylamino)-6-methylpyrazino[2,3-c]-1,2,6-thiadiazine 1,7-diethyl 2,2-dioxide, 4-amino-1-[ethoxycarbonyl)methyl]-6,7-dimethylpyrazino[2,3-c]-1,2,6-thiadiazine 2,2-dioxide, 4-amino-1-[2-(N,N-diisopropylamino)ethyl]-6,6-dimethyl-6-methylpyrazino[2,3-c]-1,2,6-thiadiazine 2,2-dioxide, 4-amino-1,7-diethyl-6-methylpyrazino[2,3-c]-1,2,6-thiadiazine 2,2-dioxide, 4-amino-1-[(ethoxycarbonyl)methyl]-7-phenylpyrazino[2,3-c]-1,2,6-thiadiazine 2,2-dioxide, 4-methylamino-1,7-diethyl-6-methylpyrazino[2,3-c]-1,2,6-thiadiazine 2,2-dioxide, 4-amino-1-ethyl-6,7-bis(trifluoromethyl)pyrazino[2,3-c]-1,2,6-thiadiazine 2,2-dioxide, 4-(2-hydroxyethylamino)-1,7-diethyl-6-methylpyrazino[2,3-c]-1,2,6-thiadiazine 2,2-dioxide, 4-amino-6,7-dimethyl-1-propylpyrazino[2,3-c]-1,2,6-thiadiazine 2,2-dioxide, 4-amino-6-bromo-1-ethyl-7-phenylpyrazino[2,3-c]-1,2,6-thiadiazine 2,2-dioxide, 4-amino-1,6,7-triethylpyrazino[2,3-c]-1,2,6-thiadiazine 2,2-dioxide 4-amino-1-ethyl-6-phenyl-7-methylpyrazino[2,3-c]-1,2,6-thiadiazine 2,2-dioxide, 4-amino-1-ethyl-6-methylpyrazino[2,3-c]-1,2,6-thiadiazine 2,2-dioxide, 4-amino-6-bromo-1-ethyl-7-methylpyrazino[2,3-c]-1,2,6-thiadiazine 2,2-dioxide, 4-amino-1-ethyl-7-phenylpyrazino[2,3-c]-1,2,6-thiadiazine 2,2-dioxide, 4-amino-1-ethyl-6-methyl-7-propylpyrazino[2,3-c]-1,2,6-thiadiazine 2,2-dioxide, 4-amino-7-ethyl-6-methyl-1-propylpyrazino[2,3-c]-1,2,6-thiadiazine 2,2-dioxide, 4-amino-7-ethyl-1,6-dimethylpyrazino[2,3-c]-1,2,6-thiadiazine 2,2-dioxide, 4-amino-1-ethyl-6,7-diisopropylpyrazino[2,3-c]-1,2,6-thiadiazine 2,2-dioxide, 4-amino-1,6-diethyl-7-methylpyrazino[2,3-c]-1,2,6-thiadiazine 2,2-dioxide.

4. The composition according to claim 2 wherein said active ingredient has diuretic activity and is selected from the group consisting of 4-amino-1,7-diethyl-6-methyl-pyrazino[2,3-c]-1,2,6-thiadiazine 2,2-dioxide, 4-amino-1-ethyl-7-phenyl-pyrazino[2,3-c]-1,2,6-thiadiazine 2,2-dioxide, 4-amino-6,7-dimethyl-1-propyl-pyrazino[2,3-c]-1,2,6-thiadiazine 2,2-dioxide, 4-amino-1-ethyl-6-phenyl-7-methyl-pyrazino[2,3-c]-1,2,6-thiadiazine 2,2-dioxide, 4-amino-1,6,7-triethyl-pyrazino[2,3-c]-1,2,6-thiadiazine 2,2-dioxide, 4-amino-1-ethyl-6-methyl-1-propyl-pyrazino[2,3-c]-1,2,6-thiadiazine 2,2-dioxide, 4-amino-7-ethyl-1,6-dimethyl-pyrazino[2,3-c]-1,2,6-thiadiazine 2,2-dioxide, and 4-amino-1,7-diethyl-4-(methylamino)-6-methyl-pyrazino[2,3-c]-1,2,6-thiadiazine 2,2-dioxide.

5. The composition according to claim 2 wherein said active ingredient has bronchodilator activity and is selected from the group consisting of 4-amino-1-[(2-ethoxycarbonyl)-methyl]-7-phenylpyrazino[2,3-c]-1,2,6-thiadiazine 2,2-dioxide, 4-amino-1-ethyl-7-phenyl-pyrazino[2,3-c]-1,2,6-thiadiazine 2,2-dioxide, 4-amino-1-ethyl-6-phenyl-7-methyl-pyrazino[2,3-c]-1,2,6-thiadiazine 2,2-dioxide, 4-amino-6-bromo-1-ethyl-7-phenyl-pyrazino[2,3-c]-1,2,6-thiadiazine 2,2-dioxide, 4-amino-6-bromo-1-ethyl-7-methyl-pyrazino[2,3-c]-1,2,6-thiadiazine 2,2-dioxide, 4-amino-1-ethyl-6-methyl-pyrazino[2,3-c]-1,2,6-thiadiazine 2,2-dioxide, 4-amino-7-ethyl-1,6-dimethyl-pyrazino[2,3-c]-1,2,6-thiadiazine 2,2-dioxide, 4-amino-1,6-diethyl-7-methyl-pyrazino[2,3-c]-1,2,6-thiadiazine 2,2-dioxide, 4-amino-1,7-diethyl-4-(methylamino)-6-methyl-pyrazino[2,3-c]-1,2,6-thiadiazine 2,2-dioxide and, 4-amino-1,7-diethyl-4-hydrazino-pyrazino[2,3-c]-1,2,6-thiadiazine 2,2-dioxide.

6. The composition according to claim 2 wherein said active ingredient has platelet antiaggregation activity and is selected from the group consisting of 4-amino-1-ethyl-6-phenyl-pyrazino[2,3-c]-1,2,6-thiadiazine 2,2-dioxide, 4-amino-1-ethyl-6-phenyl-7-methyl-pyrazino[2,3-c]-1,2,6-thiadiazine 2,2-dioxide, 4-amino-1-ethyl-6,7-diphenyl-pyrazino[2,3-c]-1,2,6-thiadiazine 2,2-dioxide and 4-amino-6-bromo-1-ethyl-7-phenyl-pyrazino[2,3-c]-1,2,6-thiadiazine 2,2-dioxide.

* * * * *